| United States Patent [19] | [11] Patent Number: 4,767,542 |
|---|---|
| Worley | [45] Date of Patent: Aug. 30, 1988 |

[54] METHOD FOR DISINFECTING AQUEOUS MEDIUM WITH N,N'-DIHALO-2-IMIDAZOLIDINONES

[75] Inventor: Shelby D. Worley, Auburn, Ala.

[73] Assignee: PPG Industries, Inc., Pittsburgh, Pa.

[21] Appl. No.: 113,941

[22] Filed: Oct. 28, 1987

Related U.S. Application Data

[60] Continuation-in-part of Ser. No. 15,480, Feb. 17, 1987, abandoned, which is a division of Ser. No. 846,767, Mar. 31, 1986, Pat. No. 4,681,948.

[51] Int. Cl.$^4$ .............................................. C02F 1/50
[52] U.S. Cl. ..................................... 210/755; 162/161; 71/67; 210/764; 422/37; 514/399
[58] Field of Search ........................... 71/67; 162/161; 210/754–756, 765, 764; 422/37; 514/399

[56] References Cited

U.S. PATENT DOCUMENTS

| 3,850,920 | 11/1974 | Walles | 260/247.73 |
|---|---|---|---|
| 4,354,030 | 10/1982 | Burow et al. | 71/67 |
| 4,560,766 | 12/1985 | Girard et al. | 548/311 |
| 4,659,484 | 4/1987 | Worley et al. | 210/764 |
| 4,681,948 | 7/1987 | Worley | 210/764 |
| 4,698,165 | 10/1987 | Theyson | 210/764 |

OTHER PUBLICATIONS

"The Identity of Heilpern's 'Pinacolylthiourea' and the Preparation of Authenic 2-thiono-4,4,5,5-tetramethylimidazolidine", by R. Sayre, J. Am. Chem. Soc., 77, 6689-Δ90 (1955).

"Concerning Symmetrical Tertiary α-Dinitroparrafin", by J. Bewad, Ber., 39, 1231-1238 (1906).

"Diaziridinones (2,3-Diazacyclopropanones)", by C. A. Renner et al, J. Org. Chem., vol. 41, No. 17, pp. 2813-2819 (1976).

"Bactericidal Activities of Selected Organic N-Halamines," by D. E. Williams et al., Applied and Environmental Microbiology, vol. 53, No. 9, pp. 2082-2089, Sep. 1987.

"Synthesis and Antibacterial Activity of New N-Halamine Compounds," by S. B. Barnela et al, J. Pharmaceutical Sciences, vol. 76, No. 3, pp. 245-247, Mar. 1987.

"The Stabilities of New N-Halamine Water Disinfectants," by S. D. Worley et al., Wat. Res., vol. 21, No. 8, pp. 983-988, 1987.

"New Halamine Water Disinfectants" by S. D. Worley et al., ACS Meeting, Sep. 2, 1987 and 6th Int'l Water Chlorination Conference, May 5, 1987.

"Bactericidal Properties of an Organic N-Halamine," by E. Elder et al., 1987 ASM Annual Meeting, Mar. 3, 1987.

*Primary Examiner*—Peter Hruskoci
*Attorney, Agent, or Firm*—Irwin M. Stein

[57] ABSTRACT

N-chloro and N-bromo derivatives of 2-imidazolidinones having substituents at the 4 and 5 positions of the ring are described. More particularly, there are described dichloro, dibromo-, and chlorobromo- derivatives of 2-imidazolidinones having at least three substituents selected from alkyl, alkoxy, hydroxy and substituted phenyl, e.g., para-substituted phenyl, at the 4 and 5 positions on the ring. These N-halo compounds are biocides, e.g., bactericides, and are useful as disinfectants and sanitizers.

33 Claims, No Drawings

METHOD FOR DISINFECTING AQUEOUS MEDIUM WITH N,N'-DIHALO-2-IMIDAZOLIDINONES

DESCRIPTION OF THE INVENTION

The Government of the United States retains a non-exclusive, paid-up license to practice or have practiced for it the invention described herein for governmental purposes.

CROSS REFERENCE TO RELATED APPLICATIONS

This application is a continuation-in-part of my application Ser. No. 15,480, filed Feb. 17, 1987, now abandoned which was a division of my application Ser. No. 846,767, filed Mar. 31, 1986, now U.S. Pat. No. 4,681,948.

The present invention relates to novel N,N'-dihalo-2-imidazolidinone derivatives and more particularly to the use of such compounds for the control and prevention of microorganisms in aqueous media, particularly industrial water systems, potable water, swimming pools, hot tubs and waste water treatment facilities, and in sanitizing applications.

The increase in demand by industry upon water for process and cooling purposes has resulted in the reuse of available water supplies in systems such as recirculating cooling towers and closed air conditioning systems. Besides being subject to severe scaling and corrosion problems, open recirculating cooling systems are an ideal environment for the growth of microorganisms of many types. The growth of the microorganism *Legionella pneumophilia* in large air conditioning systems has been documented.

The problem of algae contamination also arises quite frequently in connection with water towers, air conditioning units, water reservoirs and tanks, ponds on farms and irrigation ditches, settling ponds, wineries, waste water sluices in paper mills, sewage disposal units, the tanks of toilets, and other applications involving water usage and storage.

Municipal water systems, swimming pools and hot tubs also provide a suitable environment for the growth of microorganisms such as algae, bacteria and protozoa. For example, the presence of *Giardia lamblia* in municipal water treatment systems has caused interruption of the supply of potable water to populated areas. Municipal water systems commonly use chlorine as a disinfectant. Private swimming pools and hot tubs are treated with various commercially available chemicals, e.g., chlorine-containing compounds such as calcium hypochlorite, to control and/or eliminate bacteria, algae and other microorganisms that tend to proliferate in such aqueous media. Other toxicants such as copper sulfate (cooling towers) and chloramines have also been used to control the growth of microorganisms; however, in many systems the use of these chemicals is not desirable because of deleterious side effects resulting from their use.

In a broad aspect of the present invention, the N,N'-dihalo-2 imidazolidinone derivatives described herein are used to disinfect water and hard surfaces. These organic compounds have properties which make them a desirable source of positive halogen for the aforesaid purposes. Most are solids at room temperature and show good stability both in the dry form and in water. They are safe to handle and contain a relatively high percentage of halogen.

DETAILED DESCRIPTION OF THE INVENTION

The N,N'-dihalo-2-imidazolidinones described herein are five membered ring compounds that may be represented by the following graphic formula I:

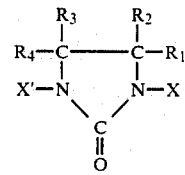

wherein X and X' are each halogen selected from the group chlorine and bromine, $R_1$, $R_2$, $R_3$ and $R_4$ are each selected from the group consisting of hydrogen, $C_1$-$C_4$ alkyl, e.g., $C_1$-$C_3$ alkyl, $C_1$-$C_4$ alkoxy, e.g., $C_1$-$C_3$ alkoxy, hydroxy and substituted phenyl, particularly para-substituted phenyl, wherein said phenyl substituents are each selected from the group consisting of $C_1$-$C_4$ alkyl, $C_1$-$C_4$ alkoxy and hydroxy; provided, however, that not more than one of the substituents $R_1$-$R_4$ is hydrogen; provided, still further, that when both X and X' are chlorine, not more than three of the substituents $R_1$, $R_2$, $R_3$ and $R_4$ are methyl.

Suitably, when X and X' are bromine, the substituents $R_1$-$R_4$ are each selected from the group $C_1$-$C_3$ alkyl, $C_1$-$C_3$ alkoxy, hydroxy and para-substituted phenyl, said paraphenyl substituents each being selected form the group $C_1$-$C_4$ alkyl, $C_1$-$C_4$ alkoxy and hydroxy.

Further, when X is chlorine and X' is bromine, the substituents $R_1$-$R_4$ are each selected from the group $C_1$-$C_3$ alkyl, $C_1$-$C_3$ alkoxy, hydroxy and para-substituted phenyl, said para-phenyl substituents each being selected from the group $C_1$-$C_4$ alkyl, $C_1$-$C_4$ alkoxy and hydroxy.

When both X and X' are chlorine, novel, N,N'-dihalo-2-imidazolidinones of the present invention include those compounds wherein (a) $R_1$, $R_2$ and $R_3$ are each selected from the group hydrogen, $C_1$-$C_4$ alkyl, e.g., $C_2$-$C_4$ alkyl, $C_1$-$C_4$ alkoxy, hydroxy and substituted phenyl, said phenyl substituents being selected from the group $C_1$-$C_4$ alkyl, $C_1$-$C_4$ alkoxy or hydroxy, and $R_4$ is selected from the group hydrogen, $C_2$-$C_4$ alkyl, $C_1$-$C_4$ alkoxy, hydroxy and substituted phenyl, said phenyl substituents being selected from the group $C_1$-$C_4$ alkyl, $C_1$-$C_4$ alkoxy or hydroxy and (b) not more than one of the substituents $R_1$-$R_4$ is hydrogen. More particularly, when both X and X' are chlorine, (a) the substituents $R_1$-$R_4$ are each selected from the group hydrogen, $C_1$-$C_3$ alkyl, $C_1$-$C_4$ alkoxy, e.g., $C_1$-$C_3$ alkoxy, hydroxy and substituted phenyl, e.g., para-substituted phenyl, said phenyl substituents being defined hereinabove, and (b) not more than one of the substituents $R_1$-$R_4$ is hydrogen.

The alkyl substituents attached to the ring of the 2-imidazolidinone compounds or to the phenyl substituent may contain from 1 to 4 carbon atoms; namely, methyl, ethyl, propyl, isopropyl and the butyls, e.g., n-butyl, isobutyl, and secondary butyl. Similarly, the alkoxy substituents attached to the ring or the phenyl substituent may contain from 1 to 4 carbon atoms; namely, methoxy, ethoxy, propoxy, isopropoxy and butoxy, e.g., n-butoxy, isobutoxy, and secondary butoxy.

Novel N,N'-dihalo-2-imidazolidinones of the present invention include those in which at least 3 of the 4 substituents (namely $R_1$–$R_4$) on the carbon atoms at the 4 and 5 positions of the ring are chosen from the described alkyl, alkoxy, hydroxy, or substituted phenyl substituents. Preferably, all four of the substituents are chosen from said group of substituents. Thus, the novel N,N'-dihalo-2-imidazolidinone derivatives contemplated herein are tri- and tetra-substituted N,N'-dihalo-2-imidazolidinones. More preferably, the $R_1$–$R_4$ substituents and the phenyl substituents are $C_1$–$C_2$ alkyl groups, i.e., methyl and ethyl groups. Still more preferably, $R_1$–$R_4$ are methyl groups.

Examples of the aforedescribed organic compounds include but are not limited to: 1-bromo-3-chloro-4,4,5,5-tetramethyl-2-imidazolidinone; 1,3-dichloro-4,4,5-trimethyl-2-imidazolidinone; 1,3-dichloro-4-methoxy-4,5,5-trimethyl-2-imidazolidonone; 1,3-dibromo-4,4,5,5-tetramethyl-2-imidazolidinone; 1,3-dichloro-4-hydroxy-4,5,5-trimethyl-2-imidazolidinone; 1,3-dichloro-4-ethyl-4,5,5-trimethyl-2-imidazolidinone; 1,3-dichloro-4,4-diethyl-5,5-dimethyl-2-imidazolidinone; and 1,3-dichloro-4,4,5,5-tetraethyl-2-imidazolidinone.

By substitution of other named substituents for $R_1$–$R_4$, e.g., ethyl, propyl, butyl, methoxy, ethoxy, propoxy, hydroxy, paramethylphenyl, etc. for one or more of the trimethyl or tetramethyl derivatives above named, other correspondingly named N,N'-dichloro-, dibromo- or chlorobromo-2-imidazolidinone derivatives may be named.

N,N'-dihalo-2-imidazolidinone derivatives of the present invention may be prepared by reacting the corresponding unhalogenated 2-imidazolidinone with a source of chlorine, bromine or, in the case of N-chloro- N'-bromo- derivatives, first a source of chlorine and then a source of bromine. While elemental chlorine and bromine may be utilized, milder chlorinating/brominating agents may be used. Examples thereof include N-chlorosuccinimide, N-bromosuccinimide, calcium hypochlorite, sodium hypochlorite, tertiary butyl hypochlorite, trichloroisocyanuric acid, N-chloroacetamide, N-chloro- or bromo-amines, etc. Halogenation of the unhalogenated 2-imidazolidinones may be accomplished in mixtures of water and common inert organic solvents, e.g., methylene chloride, chloroform and carbon tetrachloride, at room temperatures. Inert organic solvents may be used alone with N-halamine halogenating reagents. Formation of N,N'-dihalo-2-imidazolidinone may further be accomplished in situ in aqueous medium in the absence of inert organic solvent by admixing the unhalogenated 2-imidazolidinone with a source of halogen, e.g., chlorine or bromine, such as the halogenating agents described hereinbefore. Particularly contemplated unhalogenated 2-imidazolidinones include: 4,4,5,5-tetramethyl-2-imidazolidinones, 4,4,5-trimethyl-2-imidazolidinones and their ethyl analogues, 4,4-dimethyl-5,5-diethyl-2-imidazolidinones and 4-ethyl5,5-dimethyl-2-imidazolidinone.

Unhalogenated tetraalkyl substituted 2-imidazolidinones may be prepared by first reducing the corresponding 2,3-dialkyl-2,3-dinitrobutane, e.g., 2,3-dimethyl-2,3-dinitrobutane, to the 2,3-dialkyl-2,3-diaminobutane, e.g., 2,3-dimethyl-2,3-diaminobutane, and then forming the 2-imidazolidinone by reacting the 2,3-dialkyl-2,3-diaminobutane with phosgene in basic solution. Such reduction step may be accomplished by the method described by J. Bewad, in the article, Concerning Symmetrical Tertiary alpha Dinitroparrafin, *Ber.*, 39, 1231–1238 (1906). The 2-imidazolidinone may be synthesized by the method described by R. Sayre in the article, "The Identity of Heilpern's 'Pinacolylthiourea' and the preparation of Authentic 2-Thiono-4,4,5,5-tetramethylimidazolidine", *J. Am. Chem. Soc.*, 77, 6689–6690 (1955). It is contemplated that other described 2-imidazolidinone derivatives may be prepared from the corresponding 1,2-substituted-1,2-diaminoethanes, or by other organic synthetic routes known to those skilled in the art. For example, it is contemplated that 1,3-dichloro-4-methoxy-4,5,5-trimethyl-2-imidazolidinone may be prepared by cyclizing 2-methyl-3-methoxy-2,3-diaminobutane and chlorinating the resulting 4-methoxy-4,5,5-trimethyl-2-imidazolidinone. Similarly, it is contemplated that 1,3-dichloro-4-hydroxy-4,5,5-trimethyl-2-imidazolidinone may be prepared by cyclizing 2-methyl-3-hydroxy-2,3-diaminobutane and chlorinating the resulting 4-hydroxy-4,5,5-trimethyl-2-imidazolidinone.

N,N'-dihalo-2-imidazolidinone derivatives may be used for disinfecting aqueous media containing undesired microorganisms, particularly halogen sensitive microorganisms, by treating the aqueous medium with a biocidally effective amount of the 2-imidazolidinone compound. They may also be provided within an aqueous medium as a source of halogen for use against such microorganisms with which the aqueous medium comes into contact or to which the aqueous medium is applied. N,N'-dihalo-2-imidazolidinones useful in the disinfection and sanitizing applications contemplated herein may be represented by the graphic formula:

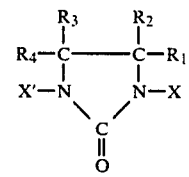

wherein X and X' are each halogen selected from the group chlorine and bromine, $R_1$, $R_2$, $R_3$, $R_4$ are each selected from the group consisting of hydrogen, $C_1$–$C_4$ alkyl, $C_1$–$C_4$ alkoxy, hydroxy and substituted phenyl, e.g., para-substituted phenyl, wherein said phenyl substituents are each selected from the group consisting of $C_1$–$C_4$ alkyl, $C_1$–$C_4$ alkoxy, and hydroxy, provided, however, that not more than one of the substituents $R_1$–$R_4$ is hydrogen.

The N,N'-dihalo-2-imidazolidinone derivatives described herein for use in disinfecting aqueous media containing undesired microorganisms may be used in combination with other sources of active halogen, e.g., chlorine or bromine. Such additional sources of active halogen may be used prior to, subsequent or simultaneously with the use of the aforesaid 2-imidazolidinones. Examples of such other sources of halogen include, but are not limited to, elemental chlorine, elemental bromine, alkali metal hypochlorite, e.g., sodium or potassium hypochlorite, calcium hypochlorite, tertiary butyl hypochlorite, and N-halogenated organic compounds which release active halogen, e.g., chlorine, when contacted with water, such as N-halamine compounds, e.g., N-chloramine or N-bromamine compounds. Further examples of N-halogenated organic compounds include the chloro- and bromo-derivatives of N-halo-succinimide, N,N'-dihalo-dimethylhydantoin, e.g., N,N'-dichlorodimethyl hydantoin alkali metal, e.g., sodium or potassium, N,N'-dihalocyanurate, e.g., sodium N,N'-dichlorocyanurate, trihaloisocyanuric acid, e.g., trichloroisocyanuric acid, N-halo-2-oxazolidinones, e.g., N-chloro- or N-bromo-2-oxazolidinones, and haloglycolurils, e.g., bromo and chloroglycolurils such as tetrachloroglycoluril and 1,3,4,6-tetrachloro-3a,6a-dimethyl glycoluril.

In a further embodiment of the present invention, it is contemplated that aqueous media may be disinfected or provided with a source of chlorine that is used as a disinfectant by admixing in the aqueous media, non-halogenated 2-imidazolidinone corresponding to the compounds of graphic formula II, i.e., compounds represented by graphic formula III:

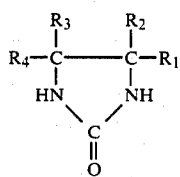

wherein $R_1$, $R_2$, $R_3$, $R_4$ are each selected from the group consisting of hydrogen, $C_1$–$C_4$ alkyl, $C_1$–$C_4$ alkoxy, hydroxy and substituted phenyl, e.g., para-substituted phenyl, said phenyl substituents being selected from the group consisting of $C_1$–$C_4$ alkyl, $C_1$–$C_4$ alkoxy and hydroxy, provided that not more than one of the substituents $R_1$–$R_4$ is hydrogen, and (b) a source of halogen selected from the group consisting of chlorine and bromine, whereby to form in situ the corresponding N,N'-dihalo-2-imidazolidinone derivative. Sources of chlorine and bromine that may be employed include, but are not limited to elemental chlorine, elemental bromine, sodium hypochlorite, calcium hypochlorite, tertiary butyl hypochlorite and N-halogenated organic compounds (N-halamines) that release their halogen in contact with water and that are less stable under the conditions of disinfection (temperature and pH) than the N,N'-dihalo-2-imidazolidinone formed in situ. Examples of such N-halogenated organic compounds are described hereinbefore.

The amount of halogen admixed with the 2-imidazolidinone of formula III may vary. Since the halogen and 2-imidazolidinone may be expected to combine in equimolar amounts, efficient use of the 2-imidazolidinone is attained by utilizing at least a stoichiometric amount of the halogen source. Preferably, sufficient of the 2-imidazolidinone and halogen source is used to form in situ a biocidal amount of the corresponding N,N'-dihalo-2-imidazolidinone.

When more than a stoichiometric amount of halogen is mixed with the 2-imidazolidinone, it is expected that the excess halogen will serve as a disinfectant for the aqueous medium in addition to the N,N'-dihalo-2-imidazolidinone formed in situ. When less than a stoichiometric amount of halogen is mixed with the 2-imidazolidinone, inefficient use of the 2-imidazolidinone (which is likely the more expensive material) results. N,N'-dihalo-2-imidazolidinone that is formed in this circumstance will serve as a disinfectant for the aqueous medium to the extent that it is present.

The 2-imidazolidinone may be added to aqueous media containing a source of halogen, or the 2-imidazolidinone may be added first to the aqueous media followed by addition of the source of halogen thereto. Still further, both may be added in desired amounts simultaneously. In the first case, the amount of available halogen in the aqueous media may be determined by analytical techniques known in the art, e.g., by use of wet chemical analysis and by use of the Palin DPD test, and the amount of 2-imidazolidinone required readily calculated.

Generally, sufficient of the N,N'-dihalo-2-imidazolidinone derivative (preformed or formed in situ) of graphic formula II is used to provide between about 0.3 and about 10 parts of potential positive halogen, e.g., chlorine, per million parts of the aqueous medium, preferably between about 1 and 2 parts of potential positive halogen per million parts of the aqueous medium. Such amounts of said 2-imidazolidinone derivatives are typically sufficient to provide a biocidal effect in the aqueous medium. The amount of potential positive halogen, e.g., chlorine, furnished by the N,N'-dihalo-2-imidazolidinone derivative corresponds to the theoretical amount of halogen that is available from the N,N'-dihalo-2-imidazolidinone derivative used. Stated in another way, usually between 1 and 30 parts of the N,N'-dihalo-2-imidazolidinone derivative per million parts of aqueous medium are used to provide a biocidal amount.

Undesired microorganisms present in an aqueous medium or on surfaces which require sanitizing include algae, fungi, bacteria, protozoa, viruses and other such organisms. Generally, the organisms that may be controlled or eliminated from the aqueous medium by use of the aforedescribed compounds or method are those which are sensitive to control or destruction by halogen or halogen-containing compounds. Of the more prominent organisms, there may be mentioned bacteria such as *Legionella pneumophilia, Shigella boydii, Staphylococcus aureus, Escherichia coli, Klebsiella pneumoniae, Proteus vulgaris, Salmonella cholera-suis, Salmonella typhimurium, Serratia marcescens, Enterobacter cloacae, Staphylococcus epidermis, Pseudomonas aeruginosa,* and *Sphaerotilus natans;* protozoa such as *Giardia lamblia* and *Entamoeba invadens;* fungi such as *Candida albicans, Rhodotorula rubra, Ceratocystis coerulescens, Phanerochaete chrysosporium, Cladosporium cladosporoides;* algae such as *Selenastrum capricornutum, Chlamydomonas reinhardtii, Chlorella pyrenoidosa, Oscillatoria prolifera, Oscillatoria lutea,* and *Anabaena cylindrica;* and viruses such as *herpesvirus, rotavirus* and *poliovirus.*

In accordance with one embodiment of the present invention, halogen-sensitive bacteria are particularly susceptible to removal by the hereindescribed method by treating the habitat of the bacteria with a bactericidal amount of a N,N'-dihalo-2-imidazolidinone derivative described herein. Similarly, when the microorganism is a protozoa, virus or fungus, the quantity of N,N'-dihalo-2-imidazolidinone derivative required may be expressed as a protozoacidal, virucidal or fungicidal amount. In the case of algae, the quantity of N,N'-dihalo-2-imidazolidinone derivative required may be expressed as an algaestatic amount.

N,N'-dihalo-2-imidazolidinone derivatives described herein may be employed in a variety of bleaching, disinfecting, sanitizing and other biocidal applications. These N,N'-dihalo-2-imidazolidinone derivatives have a relatively high halogen content and may be used in those applications which require the reduction in the number of or the control of microorganisms in an aqueous medium or on the surface of solid objects to a safe level. They may also be used as adjuvants in various biologically-active compositions such as fungicides, algaecides, bactericides, virucides and protozoacides. Of particular interest is the utility of these compounds for inhibiting the growth of microorganisms such as bacteria, algae, viruses and protozoa in industrial cooling towers, closed circuit air conditioning systems and swimming pools, or to control the number of these organisms within acceptable limits with respect to health and sanitation standards.

It will be understood, of course, that N,N'-dihalo-2-imidazolidinone derivatives described herein may be used in diverse liquid and solid formulations, including formulations in the physical state of finely-divided powders and granular materials, liquids such as solutions, concentrates, emulsifiable concentrates, slurrys and the like. The formulation and physical state will depend upon the application intended. These compounds may be used alone or in combination with other known biologically-active materials.

Thus, it will be appreciated that the N,N'-dihalo-2-imidazolidinone derivatives described herein may be used to form biologically-active compositions containing such compounds as essential ingredients thereof, which compositions may also include without limitation finely-divided dry or liquid diluents, extenders, fillers, conditioners, including various clays, phosphates, silicates, diatomaceous earth, talc, alumina-silica materials, liquid extenders, solvents, diluents or the like including water and various organic liquids such as chlorinated benzenes, acetone, cyclohexanone, xylenes, chlorinated xylene, carbon disulfide, carbon tetrachloride, ethylene dichloride, and various mixtures thereof.

One of the most advantageous applications of the N,N'-dihalo-2-imidazolidinone derivatives described herein is in compositions useful in bleaching, sterilizing and detergent applications. Hence, it will be understood that the aforesaid compounds are useful when mixed with water and in certain instances with other liquids to yield material suitable for bleaching, sterilizing and disinfecting such as in the treatment of food containers, e.g., metal and other type containers used in the transport of food products such as milk, cream and the like, in detergents for use in hospitals and other places such as hotels and restaurants for dishwashing and the like where a product having a relatively high available halogen content is desirable, as well as in compositions used as hard surface cleaners or sanitizers, e.g., for hospital floors and tables, and toilet bowl cleaners.

When liquid formulations are employed or dry materials prepared which are to be used in liquid form, it is desirable in certain instances additionally to employ a wetting, emulsifying, or dispersing agent to facilitate use of the formulation. Such agents include: alkyl aryl sulfonates, e.g., sodium dodecylbenzene sulfonate, alkyl phenoxy ethylene alkanols, alkyl aryl polyether alcohols, or other similar wetting agents or surface active materials. Soaps, fillers, abrasives, and water softening agents of the organic or inorganic type may be incorporated as desired to provide specific properties required in particular applications.

It is particularly contemplated that the N,N'-dihalo-2-imidazolidinone derivatives described herein may be used advantageously as a swimming pool sanitizer. The compounds provide a sanitizing effect over a long period of time without replenishment of the compound. As swimming pool sanitizers, the N,N'-dihalo-2-imidazolidinone derivatives may be used in amounts that provide satisfactory disinfecting levels of potentially available positive halogen, e.g., within the range of 0.3 to 1.0 part of halogen, e.g., chlorine, per million parts of water with a preferred range of between about 0.4 and about 0.8 parts of potential available positive halogen, e.g., chlorine, per million parts of water (ppm). The potential positive chlorine supplied by the N,N'-dihalo-2-imidazolidinone derivatives is available for a long period of time, and the bactericidal and disinfecting activity provided by such compounds is continuously effective during that time.

In swimming pool applications, the N,N'-dihalo-2-imidazolidinone derivatives may be used in combination with other pool additives such as buffering agents, e.g., sodium carbonate, which may be added to maintain the desired pH level of the pool. The 2-imidazolidinone derivatives are also compatible with and may be used in combination with conventional swimming pool sanitizers such as calcium hypochlorite and the halogenated isocyanurates. When used in combination with such sanitizers, the N,N'-dihalo-2-imidazolidinone derivatives provide long lasting bactericidal and disinfecting activity following the rapid sanitizing effect of the hypochlorite.

The present process is more particularly described in the following examples which are intended as illustrative only since numerous modifications and variations therein will be apparent to those skilled in the art.

EXAMPLE 1

(Preparation of 4,4,5,5-Tetramethyl-2-Imidazolidinone)

17.6 Grams (0.1 mole) of 2,3-dimethyl-2,3-dinitrobutane and 150 milliliters of concentrated hydrochloric acid were mixed in a reaction flask and immersed in a water bath maintained at 50°–60° C. 75 Grams (0.63 mole) of 20 mesh granular tin was added gradually to the reaction flask over a period of 2 hours. The contents of the reaction flask were heated under reflux for 15 minutes and the reaction mixture then made strongly alkaline by the addition of 150 milliliters of 10 Normal sodium hydroxide. 100 Milliliters of water were added to the alkaline reaction mixture which was then steam distilled. The product, i.e., 2,3-dimethyl-2,3-diaminobutane, distilled over in the first 350 milliliters of distillate.

20 Milliliters of 10 Normal sodium hydroxide solution was added to the 350 milliliters of distillate containing the 2,3-dimethyl-2,3-diaminobutane, and the resulting alkaline mixture made slightly acidic by bubbling phosgene into the solution at a rate of about 3 bubbles per second while stirring the reaction mixture at room temperature, i.e., about 25° C. 4,4,5,5-Tetramethyl-2-imidazolidinone precipitated from the reaction mixture as a white solid. The solid product was recovered by filtration and purified by recrystallization from water. The product was found to have a melting point range of 288°–289° C.

EXAMPLE 2

(Preparation of 1,3-dichloro-4,4,5,5-tetramethyl-2-imldazolidinone)

3 Grams of 4,4,5,5-tetramethyl-2-imidazolidinone was dissolved in 120 milliliters of water and the solution placed in a sealed glass vessel. Chlorine gas was introduced into the vessel until the pressure therein was in the range of 15–20 pounds per square inch. The reaction vessel was maintained in an ice bath, i.e., about 5° C., for 2 to 3 hours. 4 grams of a white crystalline solid precipitated from the reaction mixture. The white solid was recovered from the liquid reaction mixture by filtration, dried and purified by recrystallization from hexane. Elemental analysis of the product (1,3-dichloro-4,4,5,5-tetramethyl-2-imidazolidinone) gave the following results: (calculated/found) carbon 39.83/39.98, % hydrogen 5.730/5.735, % nitrogen 13.27/13.24, % chlorine 33.59/33.48, % oxygen 7.58/7.25. The product was found to have a solubility in water ranging from 0.058 grams in 100 milliliters of water at 4° C. to 0.111 grams in 100 milliliters of water at 32° C. The product had a melting point of 100° C.±2° C. Analysis of the product by proton NMR and infrared spectroscopy yielded the following results: $^1$H NMR (CDCl$_3$) $\delta$=1.29(S, 12H); IR (KBr) 2988, 1735, 1390, 1286, 1159 cm$^{-1}$. The purified product was stored in an open container for 300 days and in a closed container for 560 days at room temperature. In both cases, there was no apparent loss of total chlorine over the test period within experimental error (±5% for iodometric titrations).

EXAMPLE 3

The stability of 1,3-dichloro-4,4,5,5-tetramethyl-2-imidazolidinone (Compound A) in organic demand-free water was determined at 22° C. and pH values of 4.5, 7.0, and 9.5; and at 37° C. and pH values of 7.0 and 9.5, and the results compared to free chlorine (supplied by calcium hypochlorite). Organic demand-free water (DFW) is prepared by treating distilled, deionized water with chlorine and sunlight to remove completely any organic load present in the water. In these experiments, Compound A and calcium hypochlorite were separately dissolved in DFW (buffered to the appropriate pH) at a concentration of 10 milligrams per liter potential positive chlorine. The test solutions were placed in separate flasks, which were stoppered with porous, sterile cotton plugs. Aliquots were withdrawn each week and the percent positive chlorine remaining determined in triplicate by standard iodometric titration. Results are tabulated in Table I.

TABLE I

Percent Chlorine Remaining

| | Temp. = 22° C. | | | | | | Temp. = 37° C. | | | |
|---|---|---|---|---|---|---|---|---|---|---|
| | pH | | | | | | | | | |
| | 4.5[a] | | 7.0[b] | | 9.5[c] | | 7.0 | | 9.5 | |
| | Compound | | | | | | | | | |
| Time, Wks. | A | B | A | B | A | B | A | B | A | B |
| 1 | 99.2 | 91.8 | 97.3 | 91.8 | 95.8[e] | 88.9 | 97.4 | 83.0 | 92.8 | 90.3 |
| 2 | 100.0 | 86.2 | 95.8 | 85.0 | 95.4 | 79.0 | 93.8 | 72.0 | 85.8 | 77.8 |
| 3 | 96.3 | 80.8 | 94.3 | 79.6 | 94.7 | 71.2 | 91.5 | 57.4 | 77.2 | 66.3 |
| 4 | 95.3 | 76.4 | 92.7 | 70.6 | 93.5 | 60.3 | 87.7 | 37.1 | 72.6 | 52.9 |
| 5 | 93.7 | 71.5 | 92.6 | 63.4 | 90.8 | 50.1 | 85.9 | 29.1 | 65.4 | 45.8 |
| 6 | 92.6 | 65.0[d] | 92.5 | 54.7[d] | 87.2 | 38.5[d] | 83.7 | 14.8 | 51.8 | ND |

[a]0.05 Molar Acetate Buffer
[b]0.05 Molar Phosphate Buffer
[c]0.01 Molar Borate/NaOH Buffer
[d]6 weeks plus 1 day
[e]1 week plus 1 day
A = 1,3-dichloro-4,4,5,5-tetramethyl-2-imidazolidinone
B = Calcium Hypochlorite
ND = No Determination The data of Table I demonstrates that at both 22° C. and 37° C., Compund A is more stable than calcium hypochlorite at all of the pHs tested.

EXAMPLE 4

A synthetic organic demand water was prepared by mixing the following reagents with organic demand-free water (DFW): 375 milligrams per liter of each of the inorganic salts, calcium chloride, magnesium chloride, potassium chloride, and sodium chloride; 50 milligrams per liter of bentonite clay; 30 milligrams per liter of humic acid; 0.01 percent final concentration of heat-treated horse serum; and 5×10$^5$ cells per milliliter of heat-killed *Saccharomyces cerevisiae*. Compound A and calcium hypochlorite were added to separate vessels containing the aforedescribed synthetic organic demand water (WCW) in amounts to provide a concentration of 10 milligrams per liter of potential positive chlorine. The WCW was buffered with 0.01 Molar borate/sodium hydroxide buffer to a pH of 9.5 and cooled to 4° C. Aliquots were withdrawn periodically and the percent positive chlorine remaining was determined in triplicate by standard iodometric titration. Results are tabulated in Table II.

TABLE II

Percent Chlorine Remaining
in the Presence of Organic Demand

Temp. = 4° C.; pH = 9.5
(Compound)

| Time, Hrs. | A | B |
|---|---|---|
| 0.5 | 98.1 | 51.5 |
| 1.0 | 96.8 | 46.4 |
| 2.0 | 96.3 | ND |
| 2.5 | ND | 39.6 |
| 4.0 | 93.6 | ND |
| 4.2 | ND | 39.6 |
| 7.0 | 92.6 | ND |
| 7.5 | ND | 36.2 |
| 24.0 | 89.9 | 31.3 |
| 48.0 | ND | 25.4 |
| 49.0 | 83.0 | ND |
| 73.0 | 80.9 | ND |
| 76.5 | ND | 21.5 |

ND = No Determination

The data of Table II show that Compound A is much more stable than calcium hypochlorite in synthetic organic demand water over a period of about 3 days.

EXAMPLE 5

1.42 Grams (0.01 moles) of 4,4,5,5-tetramethyl-2-imidazolidinone was suspended in 32 milliliters of a 1 Molar sodium hydroxide solution contained in a glass reaction vessel. The suspension was warmed briefly to enhance solubility, cooled to 0° C. in an ice bath, and 3.49 grams (0.0218 moles) of liquid bromine added dropwise with stirring over a 15 minute period at 0° C. The reaction mixture was stirred for 2-3 hours additional at ice-bath temperatures. A pale yellow solid product was produced, which was recovered by filtration, washed with cold water, and dried. Purification of the product was accomplished by crystallization from cyclohexane. 1.9 Grams of 1,3-dibromo-4,4,5,5-tetramethyl-2-imidazolidinone was obtained. Elemental analysis of the product yielded the following results: (calculated/found) % carbon 28 00/28.11, hydrogen 4.00/4.04, % nitrogen 9.33/9.23, % bromine 53.33/53.29. The purified product is a pale yellow crystalline solid with a water solubility ranging from 0.130 grams in hundred milliliters of water at 4° C. to 0.225 grams in 100 milliliters of water at 32° C. Water solutions of the product are colorless and odorless. The purified product was found to have a melting point range of 119°–121° C. Proton NMR and infrared spectroscopy analysis yielded the following: $^1$H NMR (CDCl$_3$) $\delta = 1.23$ (S, 12 H); IR (KBr) 2977, 1715, 1391, 1288, 1157 cm$^{-1}$. The purified product was stored in an open container for 300 days and in a closed container for 560 days at room temperature. In both cases, there was no apparent loss of total bromine over the test period within experimental error ($\pm 5\%$ for iodometric titrations).

EXAMPLE 6

In accordance with the procedure of Example 3, the stability of 1,3-dibromo-4,4,5,5-tetramethyl-2-imidazolidinone (Compound C) in DFW at 22° C. and at three pH conditions was determined and compared to calcium hypochlorite. In these tests, Compound C was dissolved in DFW at a concentration of 22.5 milligrams per liter of potential positive bromine. Calcium hypochlorite was dissolved in DFW at a concentration of 10 milligrams per liter of potential positive chlorine. The aforesaid concentrations represent the same molar halogen concentration for each compound. The test solutions were placed in flasks which were stoppered with porous, sterile cotton plugs. Aliquots were withdrawn each week and the percent positive bromine or positive chlorine remaining, as the case may be, determined in triplicate by amperometric titration. Results are tabulated in Table III.

TABLE III

| | Percent Halogen Remaining (22° C.) | | | | | |
|---|---|---|---|---|---|---|
| | pH | | | | | |
| | 4.5$^a$ | | 7.0$^b$ | | 9.5$^c$ | |
| | Compound | | | | | |
| Time, Wks. | C | B | C | B | C | B |
| 1 | 95.0 | 91.8 | 96.6 | 91.8 | 96.5$^e$ | 88.9 |
| 2 | 94.9 | 86.2 | 95.1 | 85.0 | ND | 79.0 |
| 3 | 94.2 | 80.8 | 87.6 | 79.6 | 92.0 | 71.2 |
| 4 | 90.9 | 76.4 | 95.4 | 70.6 | 89.6 | 60.3 |
| 5 | 89.9 | 71.5 | 81.7 | 63.4 | 87.1 | 50.1 |
| 6 | 88.8 | 65.0$^d$ | 77.3 | 54.7$^d$ | 82.3 | 38.5$^d$ |

$^a$0.05 Molar Acetate Buffer
$^b$0.05 Molar Phosphate Buffer
$^c$0.01 Molar Borate/NaOH Buffer
$^d$6 weeks plus 1 day
$^e$1 week plus 1 day
C = 1,3-dibromo-4,4,5,5-tetramethyl-2-imidazolidinone
B = Calcium Hypochlorite
ND = No Determination The data of Table III demonstrate that Compound C is significantly more stable than calcium hypochlorite over the measured period at 22° C. at the pH values, 4.5, 7.0 and 9.5 in DFW. At 37° C., Compound C was found to be less stable in DFW than calcium hypochlorite at this higher temperature and at the aforesaid three pH values.

In synthetic organic-demand water (WCW), Compound C is approximately equal in stability to free chlorine from calcium hypochlorite—both having a half-likfe of approximately 60 minutes.

It appears from the above data and that of Examples 3 and 4 that Compound C is less stable at high temperatures, e.g., 37° C., than Compound A. It further appears that Compound C is more reactive in the presence of an organic load than the corresponding chlorinated compound (Compound A).

EXAMPLE 7

0.3 Grams (2.11 millimoles) of 4,4,5,5-tetramethyl-2-imidazolidinone was added to a reaction flask containing 12 milliliters of methylene chloride and 0.24 grams (2.21 millimoles) of tertiary butyl hypochlorite. The resulting suspension was stirred at room temperature, i.e., about 25° C., for 3 hours. Light was excluded from the flask by wrapping it with an opaque material. The progress of the chlorination reaction was monitored by spotting small aliquots on a thin layer chromatography plate and eluting with methylene chloride. The chlorination reaction was terminated when a spot corresponding to the dichloro analog, i.e., 1,3-dichloro-4,4,5,5-tetramethyl-2-imidazolidinone, first appeared. The reaction mixture was then filtered to remove unreacted starting material and the filtrate evaporated on a rotary evaporator to yield 0.312 grams of the monochloro derivative, i.e., 1-chloro-4,4,5,5-tetramethyl-2-imidazolidinone. The monochloro derivative was purified of any dichloro analog by passing the crude product through a silica gel column and separating the dichloro analog by eluting the column with methylene chloride. The monochloro analog may be eluted from the column using diethyl ether. The aforesaid synthesis of the monochloro derivative was repeated to obtain a sufficient quantity thereof to continue with the following synthesis.

0.50 Grams (2.83 millimoles) of the monochloro derivative was added to 0.51 grams (2.86 millimoles) of N-bromosuccinimide in 5 milliliters of methylene chloride. The reaction mixture was stirred for from 2 to 3 hours at room temperature (about 25° C). The progress of the reaction was monitored by spotting a small aliquot of the reaction mixture on a thin layer chromatography plate and eluting with methylene chloride. After the reaction was complete, the solvent was evaporated on a rotary evaporator. The crude product, 1-bromo-3-chloro-4,4,5,5-tetramethyl-2-imidazolidinone, was purified of N-bromosuccinimide by use of column chromatography (silica gel column-methylene chloride eluent). The resulting product was further purified by crystallization from cyclohexane and submitted for elemental analysis, which yielded: (calculated/found), % carbon 32.94/32.90, % hydrogen 4.70/4.75, % nitrogen 10.98/11.00, % bromine 31.37/31.37, % chlorine 13.92/13.84. The product was a pale yellow crystalline solid having a water solubility of 0.183 grams per hundred milliliters of water at 22° C. The water solution is colorless and odorless. The product has a melting point range of 102°–104° C. Proton NMR and infrared spectroscopy yielded the following: $^1$H NMR (CDCl$_3$) $\delta = 1.23$ (S, 6H), $\delta = 1.28$ (S, 6H); IR (KBr) 2982, 1709, 1387, 1289, 1158 cm$^{-1}$.

EXAMPLE 8

In accordance with the procedure of Example 3, the stabilities of 1-bromo-3-chloro-4,4,5,5-tetramethyl-2-imidazolidinone (Compound D) and calcium hypochlorite at 22° C. and at three pHs, i.e., 4.5, 7.0 and 9.5 were compared. In these tests, calcium hypochlorite was dissolved in buffered DFW at a concentration of 10 milligrams per liter total positive chlorine and Compound D dissolved in buffered DFW at a concentration of 16.27 milligrams per liter total oxidant (potential positive chlorine and potential positive bromine). These concentrations represent the same molar halogen concentration for each compound in the buffered DFW. The solutions were stored in flasks which were stopped with porous, sterile cotton plugs. Aliquots were withdrawn each week and the percent positive chlorine (in the case of calcium hypochlorite), or the percent positive chlorine and percent positive bromine (in the case of Compound D) were determined in triplicate by amperometric or iodometric titration for calcium hypochlorite, and iodometric titration for Compound D. Results are tabulated in Table IV.

TABLE IV

| | Percent Halogen Remaining (22° C.) | | | | | |
|---|---|---|---|---|---|---|
| | pH | | | | | |
| | 4.5$^a$ | | 7.0$^b$ | | 9.5$^c$ | |
| | Compound | | | | | |
| Time, Wks. | D | B | D | B | D | B |
| 1 | 74.4 | 91.8 | 96.9 | 91.8 | 94.3 | 88.9 |
| 2 | 74.5$^d$ | 86.2 | 95.6 | 85.0 | 92.2 | 79.0 |
| 3 | 73.3$^e$ | 80.8 | ND | 79.6 | 87.7$^g$ | 71.2 |
| 4 | 71.5 | 76.4 | 85.6 | 70.6 | 83.4 | 60.3 |
| 5 | 70.2 | 71.5 | 85.4 | 63.4 | 80.6 | 50.1 |
| 6 | 67.3$^f$ | 65.0$^f$ | 84.5 | 54.7$^f$ | 73.4 | 38.5$^f$ |

$^a$0.05 Molar Acetate Buffer
$^b$0.05 Molar Phosphate Buffer
$^c$0.01 Molar Borate/NaOH Buffer
$^d$2 weeks plus 1 day
$^e$2 weeks plus 3 days
$^f$6 weeks plus 1 day
$^g$3 weeks plus 3 days
D = 1-bromo-3-chloro-4,4,5,5-tetramethyl-2-imidazolidinone
B = Calcium Hypochlorite
ND = No Determination The data of Table IV show that at a pH of 4.5, Compound D is initially less stable than calcium hypochlorite; but that its stability quickly stabilizes. At higher pHs; namely at a pH of 7.0 or 9.5, Compound D is significantly more stable than calcium hypochlorite.

EXAMPLE 9

In accordance with the procedure of Example 4, the stabilities of Compound D and calcium hypochlorite at pH 9.5 and a temperature of 4° C. in water containing a heavy organic load (WCW) were determined. Results are tabulated in Table V.

TABLE V

| | Percent Halogen Remaining in Presence of Organic Demand | |
|---|---|---|
| | Temp. = 4° C.; pH = 9.5 (Compound) | |
| Time, Hrs. | D | B |
| 0.5 | 68.3 | 51.5 |
| 1.0 | 64.2 | 46.4 |
| 4.2 | ND | 39.6 |
| 6.0 | 56.1 | ND |
| 24.0 | ND | 31.3 |
| 24.2 | 53.5 | ND |
| 76.5 | ND | 21.5 |

TABLE V-continued

| | Percent Halogen Remaining in Presence of Organic Demand | |
|---|---|---|
| | Temp. = 4° C.; pH = 9.5 (Compound) | |
| Time, Hrs. | D | B |
| 99.0 | 50.3 | ND |

ND = No Determination

The data of Table V show that Compound D is signifincantly more stable than calcium hypochlorite at the conditions tested.

EXAMPLE 10

(Preparation of 1,3-Dichloro-4,4,5-Trimethyl-2-Imidazolidinone)

Nitrosyl chloride was distilled slowly into a reaction flask containing a stoichiometric excess of anhydrous 2-methyl-2-butene while maintaining the contents of the reaction flask between about −8° and −5° C. by means of an acetone-ice slurry. The reaction solution became light blue and a white crystalline solid precipitated out of solution. The reaction mixture was allowed to stand at −5° C. for about 2 hours and then cooled to about −20° C. with an acetone-dry ice slurry. The white solid product, 2-chloro-2-methyl-3-nitrosobutane, was removed on a precooled filter, washed several times with cold methanol and dried under vacuum.

2-chloro-2-methyl-3-nitrosobutane was added slowly to a saturated absolute methanol-ammonia solution at 0° C. The mixture was allowed to stand overnight at 0° C. and then allowed to warm to room temperature. The reaction mixture was refluxed for 12 hours while passing a continuous stream of ammonia through the solution. The liquid reaction mixture was evaporated to dryness under vacuum to produce a solid. This solid was separated from ammonium chloride impurity by extraction with boiling secondary butyl alcohol. The residue from the secondary butyl alcohol extractions contained the product 2-amino-2-methyl-3-butanone oxime hydrochloride.

15.25 Grams of 2-amino-2-methyl-3-butanone oxime hydrochloride were dissolved in dry butanol contained in a 1-liter round-bottom flask equipped with a reflux condenser, and the resulting solution heated to boiling. 26 Grams of sodium were added in small pieces to the refluxing solution. The reaction mixture was refluxed for 2 hours until all of the sodium had dissolved. Upon cooling, solid sodium butoxide precipitated. 300 Milliliters of water were added to the liquid reaction mixture, which was then steamed distilled until the distillate was no longer alkaline. Then, 30 milliliters of concentrated hydrochloric acid were added to the distillate, and the acidified distillate concentrated to 70 milliliters. The concentrate contained the product 2,3-diamino-2-methylbutane as a hydrochloride.

30 Milliliters of 10 Normal sodium hydroxide were introduced into the concentrated distillate and phosgene slowly bubbled through the solution for 2 hours until the solution achieved a pH of about 7.0. The crude solid product (4,4,5-trimethyl-2-imidazolidinone) was filtered, dried, and crystallized from methylene chloride.

A glass reaction vessel was charged with 10 milliliters of a 2.35 Normal sodium hydroxide solution of one gram (0.0078 mole) of 4,4,5-trimethyl-2-imidazolidinone. The glass reaction vessel was sealed and then charged with chlorine gas to a pressure of 8-10 pounds per square inch and the reaction vessel held at that pressure at ice-bath temperatures for 30-45 minutes. Thereafter, the reaction mixture was brought to ambient temperature and the product extracted with methylene chloride. The organic layer was dried briefly over anhydrous sodium sulfate and the methylene chloride solvent removed using a rotary evaporator. The product (1,3-dichloro-4,4,5-trimethyl-2-imidazolidinone) was a colorless oil, which solidified on refrigeration. Purification of the product was performed by passing the liquid product through a silica gel column and eluting with methylene chloride.

The purified product had a melting temperature near room temperature and was soluble in water. Water solutions of the product were colorless and odorless. An elemental analysis of the product yielded the following results: (calculated/found) % carbon 36.54/35.78, % hydrogen 5.07/5.17, % nitrogen 14.21/14.17, % chlorine 36.04/36.31. Proton NMR and infrared spectroscopy analysis of the product yielded the following results: $^1$H NMR (CDCl$_3$ = 1.22 (u, 3H), = 1.33 (u, 6H), = 3.43 (q, 1H); IR (KBr) 2985, 2940, 1748, 1285 cm$^{-1}$.

EXAMPLE 11

In accordance with the procedure described in Example 3, the stability of 1,34-dichloro-4,4,5-trimethyl-2-imidazolidinone (Compound E) was tested at 22° C. at three pH values in DFW. The stability was compared with that of calcium hypochlorite. In tests, the compounds were dissolved in DFW water at a concentration fo 10 milligrams per liter of potential positive chlorine in flasks which were stoppered with porous, sterile cotton plugs. Aliquots were withdrawn each week and the percent positive chlorine remaining determined in triplicate by standard iodometric tritration. Results are tabulated in Table VI.

TABLE VI

| | Percent Chlorine Remaining (22° C.) | | | | | |
|---|---|---|---|---|---|---|
| | pH | | | | | |
| | 4.5$^a$ | | 7.0$^b$ | | 9.5$^c$ | |
| | Compound | | | | | |
| Time, Wks. | D | B | D | B | D | B |
| 1 | 98.7 | 91.8 | 94.1$^e$ | 91.8 | 88.2 | 88.9 |
| 2 | 97.9 | 86.2 | 91.3 | 85.0 | 78.4 | 79.0 |
| 3 | 97.1 | 80.8 | 88.0 | 79.6 | 73.1 | 71.2 |
| 4 | 97.3 | 76.4 | 86.9 | 70.6 | 67.8 | 60.3 |
| 5 | 95.7 | 71.5 | 82.4 | 63.4 | 58.6 | 50.1 |
| 6 | 93.6 | 65.0$^d$ | 80.1 | 54.7$^d$ | 53.6 | 38.5$^d$ |

$^a$0.05 Molar Acetate Buffer
$^b$0.05 Molar Phosphate Buffer
$^c$0.01 Molar Borate/NaOH Buffer
$^d$6 weeks plus 1 day
$^e$1 week plus 1 day
E = 1,3-dichloro-4,4,5-trimethyl-2-imidazolidinone
B = Calcium Hypochlorite The data of Table VI show that Compound E is more stable than calcium hypochlorite in organic demand-free water at 22° C. at all of the pH values tested.

EXAMPLE 12

The stability of calcium hypochlorite and Compound E were tested in accordance with the procedure of Example 4 in synthetic organic demand water at pH 9.5 and 4° C. Results are tabulated in Table VII.

TABLE VII

| Percent Chlorine Remaining in Presence of Organic Demand | | |
|---|---|---|
| pH = 9.5; Temp. = 4° C. | | |
| (Compound) | | |
| Time, Hrs. | E | B |
| 0.5 | 93.0 | 51.5 |
| 1.0 | 93.0 | 46.4 |
| 4.0 | 87.5 | ND |
| 4.2 | ND | 39.6 |
| 24.0 | 76.5 | 31.3 |
| 73.4 | 65.0 | ND |
| 76.5 | ND | 21.5 |

ND = No Determination

The data of Table VII show that Compound E is much more stable than calcium hypochlorite at the conditions tested.

EXAMPLE 13

The 2-imidazolidinone derivative compounds of Examples 2, 5, 7, and 10; namely Compounds A, C, D and E, were tested as toxicants for various organisms. In the procedure for tests against bacteria or fungi, 50 milliliters of organic demand-free buffered aqueous solutions (DFW) or buffered aqueous solutions containing a synthetic organic demand (WCW) were placed in a 125 milliliter flask and then inoculated with the organism to be tested such that the final density of the organism was about $1 \times 10^6$ cfu/ml (colony forming units per milliliter). The inoculated solution was allowed to equilibrate at the test temperature by immersion in a thermostated water bath for 15 minutes with constant stirring. Then, an appropriate amount of an aqueous solution containing the test 2-imidazolidinone compound maintained at the same test temperature was added to the inoculated solution to bring the total concentration of ionizable positive halogen, i.e., chlorine, bromine or chlorine and bromine, in the mixture to a predetermined level. (The concentrations used in separate test procedures were 10 parts per million, 5 parts per million, 2.5 parts per million, and 1 part per million for Compounds A and E, and the total halogen molar equivalents for Compounds C and D). 1 milliliter aliquots were removed from the test mixture at various predetermined times and quenched by 1 milliliter portions of sterile 0.02 Normal sodium thiosulfate. Serial dilutions of the aliquots were made into sterile saline. Then, three 25 microliter aliquots of each of the resulting dilutions were applied to the dried surface of a Petri dish containing the appropriate growth media for plating the organism under study. The three replicates for each dilution were counted and averaged. This average was used to compute the cfu/ml for that particular aliquot. Inactivation of the organism was considered to be at least 99.999 percent when no colonies were detected in the thiosulfate quenched aliquots. The CT products (the product of multiplying the test concentration in milligrams/liter of positive chlorine and the kill time in minutes) for complete kill of the various organisms were determined. Protocols for tests against protozoa may be found in the report, "New Disinfection Agents For Water" by S. D. Worley et al., available from NTIS, Report No. AD-149537. Results are tabluated in Table VIII.

TABLE VIII

CT PRODUCT VALUES

| Organism | Test Conditions | Test Compound | | | |
|---|---|---|---|---|---|
| | | A | C | D | E |
| Staphylococcus aureus | pH 7.0, 22° C., DFW | 716–1400 | 9.78 | 36.32 | 511 |
| | pH 4.5, 22° C., DFW | 1295 | 2.44 | 13.02 | 605 |
| | pH 9.5, 22° C., DFW | 522.6 | 3.28 | 14.07 | 336 |
| | pH 9.5, 4° C., DFW | 4355 | 25.13 | 651 | 1372 |
| | pH 9.5, 4° C., WCW | 9679 | 291–6270 | 174–2282 | 1292–2264 |
| Shigella boydii | pH 7.0, 22° C., DFW | 26 | 9.70 | 15.09 | ND[a] |
| | pH 9.5, 4° C., WCW | ND | 148–314 | 249–446 | ND |
| | pH 9.5, 4° C., DFW | ND | 24.82 | ND | ND |
| Ceratocystis coerulescens | pH 7.0, 25° C., DFW | 2355 | 6330 | ND | 1250 |
| Entamoeba invadens | pH 7.0, 25° C., DFW | 4–10 | <2 | ND | 2–4 |
| Giardia lamblia | pH 7.0, 25° C., DFW | 4–10 | <2 | ND | <2 |
| Legionella pneumophila | pH 7.0, 22° C., DFW | 300–600 | ND | ND | <120 |

[a]ND = No Determination

EXAMPLE 14

Compound A was added to DFW having a pH 7.0 and a temperature of 22° C. in amounts sufficient to provide a concentration of 2 milligrams per liter of potential positive chlorine. This solution was challenged with $10^6$ cfu/ml of *Staphylococcus aureus* bacteria (time 0) and then rechallenged repetitively at times 96 hours, 264 hours, 432 hours, 744 hours, 1080 hours and 1416 hours. The time required to disinfect the solution, i.e., the time required for complete disinfection for a 6 log reduction in viable organism, ranged from 90 to 240 minutes. No more challenges with the organism were made after 1416 hours; however, total disinfection by Compound A still occurred at that time. In comparison, calcium hypochlorite survived challenges only at times 0 and 72 hours at a concentration level of 1 milligram per liter of potential positive chlorine under the aforesaid conditions of temperature and pH—losing its ability to disinfect between 72 and 96 hours.

EXAMPLE 15

The procedure of Example 14 was followed using the Compound C. The solution contained 2.25 milligrams per liter of potential positive bromine and was challenged with the bacteria *S. aureus* at times 0, 72 hours, 96 hours, 120 hours and 144 hours. The solution lost its effectiveness to disinfect between 120 and 144 hours.

EXAMPLE 16

The procedure of Example 14 was followed utilizing Compound E. The solution contained 1 milligram per liter of potential positive chlorine and was challenged repetitively with $10^6$ cfu/ml of *S. aureus* at times 0, 96 hours, 264 hours, 432 hours, 744 hours, 1080 hours and 1416 hours. The solution did not lose its ability to disinfect until after the 1080 hour challenge. By comparison a 1 milligram/liter solution of potential positive chlorine from calcium hypochlorite becomes ineffective as a disinfectant between 72 and 96 hours under the same test conditions.

Although the present process has been described with reference to specific details of certain embodiments thereof, it is not intended that such details should be regarded as limitations upon the scope of the invention except as and to the extent that they are included in the accompanying claims.

What is claimed is:

1. A method for disinfecting an aqueous medium containing undesired halogen-sensitive microorganism, which comprises treating the aqueous medium with a biocidally effective amount of N,N'-dihalo-2-imidazolidinone represented by the graphic formula:

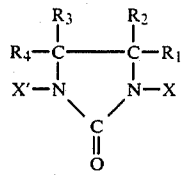

wherein X and X' are each halogen selected from the group chlorine and bromine, $R_1$, $R_2$, $R_3$ and $R_4$ are each selected from the group consisting of hydrogen, $C_1$–$C_4$ alkyl, $C_1$–$C_4$ alkoxy, hydroxy and substituted phenyl, said phenyl substituents each being selected from the group $C_1$–$C_4$ alkyl, $C_1$–$C_4$ alkoxy, and hydroxy, provided that not more than one of the substituents $R_1$–$R_4$ is hydrogen.

2. The method of claim 1 wherein $R_1$, $R_2$, $R_3$ and $R_4$ are each selected from the group methyl and ethyl.

3. The method of claim 1 wherein $R_1$, $R_2$, $R_3$ and $R_4$ are each methyl.

4. The method of claim 3 wherein the N,N'-dihalo-2-imidazolidinone is 1,3-dibromo-4,4,5,5-tetramethyl-2-imidazolidinone, 1,3-dichloro-4,4,5,5-tetramethyl-2-imidazolidinone, 1-bromo-3-chloro-4,4,5,5-tetramethyl-2-imidazolidinone, or 1,3-dichloro-4,4,5-trimethyl-2-imidazolidinone.

5. The method of claim 1 wherein the aqueous medium is found in a swimming pool, air-conditioning system, cooling tower, hot tub, or a source of potable water.

6. The method of claim 1 wherein the aqueous medium is treated also with a source of active halogen selected from the group consisting of elemental chlorine, elemental bromine, alkali metal hypochlorite, calcium hypochlorite, tertiary butyl hypochlorite, and N-halogenated organic compounds which release halogen when contacted with water.

7. The method of claim 6 wherein the N-halogenated organic compound is selected from the group consisting of chloro- and bromo- derivatives of N-halosuccinimide, N,N'-dihalo-dimethylhydantoin, sodium or potassium N,N'-dihalocyanurate, trihaloisocyanuric acid, N-halo-2-oxazolidinones and haloglycolurils.

8. A method for disinfecting an aqueous medium containing microorganism selected from the group consisting of *Legionella pneumophilia, Giardia lamblia, Entamoeba invadens, Shigella boydii* and *Staphylococcus aureus*, which comprises treating the aqueous medium with a biocidally effective amount of N,N'-dihalo-2-imidazolidinone represented by the graphic formula:

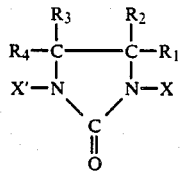

wherein X and X' are each halogen selected from the group chlorine and bromine, $R_1$, $R_2$, $R_3$ and $R_4$ are each selected from the group consisting of hydrogen, $C_1$-$C_4$ alkyl, $C_1$-$C_4$ alkoxy, hydroxy and substituted phenyl, said phenyl substituents each being selected from the group $C_1$-$C_4$ alkyl, $C_1$-$C_4$ alkoxy, and hydroxy, provided that not more than one of the substituents $R_1$-$R_4$ is hydrogen.

9. The method of claim 8 wherein $R_1$, $R_2$, $R_3$, and $R_4$ are each selected from the group methyl and ethyl.

10. The method of claim 9 wherein the aqueous medium is found in a swimming pool, air-conditioning system, cooling tower, hot tub, waste disposal facility or source of potable water.

11. The method of claim 10 wherein the N,N'-dihalo-2-imidazolidinone is 1,3-dibromo-4,4,5,5-tetramethyl-2-imidazolidinone, 1,3-dichloro-4,4,5,5-tetramethyl-2-imidazolidinone, 1-bromo-3-chloro-4,4,5,5-tetramethyl-2-imidazolidinone, or 1,3-dichloro-4,4,5-trimethyl-2-imidazolidinone.

12. A method for disinfecting an aqueous medium containing undesired halogen-sensitive microorganism, which comprises admixing in the aqueous medium (a) imidazolidinone compound represented by the graphic formula:

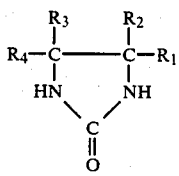

wherein $R_1$, $R_2$, $R_3$, $R_4$ are each selected from the group consisting of hydrogen, $C_1$-$C_4$ alkyl, $C_1$-$C_4$ alkoxy, hydroxy, and substituted phenyl, said substituted phenyl substituents each being selected from the group $C_1$-$C_4$ alkyl, $C_1$-$C_4$ alkoxy, or hydroxy, provided that not more than one of the substituents $R_1$-$R_4$ is hydrogen, and (b) a source of halogen, said halogen being selected from the group consisting of chlorine and bromine, whereby to form in situ a biocidal amount of the corresponding N,N'-dihalo-2-imidazolidinone derivative.

13. The method of claim 12 wherein at least a stoichiometric amount of the source of halogen is used.

14. The method of claim 12 wherein $R_1$, $R_2$, $R_3$ and $R_4$ are each methyl or ethyl.

15. The method of claim 14 wherein the aqueous medium is found in a swimming pool, air-conditioning system, cooling tower, hot tub, waste disposal facility or a source of potable water.

16. The method of claim 15 wherein the imidazolidinone compound is 4,4,5,5-tetramethyl-2-imidazolidinone or 4,4,5-trimethyl-2-imidazolidinone.

17. The method of claim 12 wherein the source of halogen is elemental chlorine, elemental bromine, sodium hypochlorite, calcium hypochlorite, tertiary butyl hypochlorite or N-halogenated organic compound that releases active halogen when contacted with water and which is less stable than the N,N'-dihalo-2-imidazolidinone derivative formed in situ.

18. The method of claim 17 wherein $R_1$, $R_2$, $R_3$ and $R_4$ are each methyl or ethyl.

19. The method of claim 18 wherein the imidazolidinone compound is 4,4,5,5-tetramethyl-2-imidazolidinone or 4,4,5-trimethyl-2-imidazolidinone.

20. The method of claim 19 wherein at least a stoichiometric amount of the source of halogen is used.

21. A method of combatting halogen-sensitive bacteria in a habitat for said bacteria comprising treating the habitat of the bacteria with a bactericidal amount of N,N'-dihalo-2-imidazolidinone represented by the graphic formula:

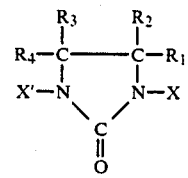

wherein X and X' are each halogen selected from the group consisting of chlorine and bromine, $R_1$, $R_2$, $R_3$ and $R_4$ are each selected from the group consisting of hydrogen, $C_1$-$C_4$ alkyl, $C_1$-$C_4$ alkoxy, hydroxy and substituted phenyl, said phenyl substituents each being selected from the group $C_1$-$C_4$ alkyl, $C_1$-$C_4$ alkoxy, and hydroxy, provided that not more than one of the substituents $R_1$-$R_4$ is hydrogen.

22. The method of claim 21 wherein $R_1$, $R_2$, $R_3$ and $R_4$ are each methyl or ethyl.

23. The method of claim 21 wherein the N,N'-dihalo imidazolidinone is 1,3-dibromo-4,4,5,5-tetramethyl-2-imidazolidinone, 1,3-dichloro-4,4,5,5-tetramethyl-2-imidazolidinone, 1-bromo-3-chloro-4,4,5,5-tetramethyl-2-imidazolidinone, or 1,3-dichloro-4,4,5-trimethyl-2-imidazolidinone.

24. A method for providing N,N'-dihalo-2-imidazolidinone in an aqueous medium, which comprises admixing in said aqueous medium (a) imidazolidinone compound represented by the graphic formula:

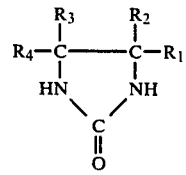

wherein $R_1$, $R_2$, $R_3$, $R_4$ are each selected from the group consisting of hydrogen, $C_1$-$C_4$ alkyl, $C_1$-$C_4$ alkoxy, hydroxy and substituted phenyl, said substituted phenyl substituents each being selected from the group $C_1$-$C_4$ alkyl, $C_1$-$C_4$ alkoxy or hydroxy, provided that not more than one of the substituents $R_1$-$R_4$ is hydrogen, and (b) a source of halogen, said halogen being selected from the group consisting of chlorine and bromine, whereby to form in situ the corresponding N,N'-dihalo-2-imidazolidinone derivative.

25. The method of claim 24 wherein $R_1$, $R_2$, $R_3$ and $R_4$ are each selected from the group methyl and ethyl.

26. The method of claim 24 wherein the source of halogen is elemental chlorine, elemental bromine, alkali metal hypochlorite, calcium hypochlorite, tertiary butyl hypochlorite, and N-halogenated organic compounds which release halogen when contacted with water.

27. The method of claim 26 wherein the N-halogenated organic compound is selected from the group consisting of chloro- and bromo- derivatives of N-halosuccinimide, N,N'-dihalo-dimethylhydantoin, sodium or potassium N,N'-dihalocyanurate, trihaloisocyanuric acid, N-halo-2-oxazolidinones and haloglcolurils.

28. The method of claim 24 wherein the imidazolidinone compound is 4,4,5,5-tetramethyl-2-imidazolidinone, or 4,4,5-trimethyl-2-imidazolidinone.

29. The method of claim 24 wherein $R_1$, $R_2$, $R_3$ and $R_4$ are each selected from the group methyl and ethyl and the source of halogen is elemental chlorine, elemental bromine, alkali metal hypochlorite, calcium hypochlorite, tertiary butyl hypochlorite, and N-halogenated organic compounds which release halogen when contacted with water.

30. The method of claim 29 wherein N,N'-dihalo-2-imidazolidinone is formed in said aqueous medium in amounts sufficient to be biocidally effective against halogen-sensitive microorganisms.

31. The method of claim 29 wherein the imidazolidinone compound is 4,4,5,5-tetramethyl-2-imidazolidinone, or 4,4,5-trimethyl-2-imidazolidinone.

32. The method of claim 31 wherein the N-halogenated organic compound is selected from the group consisting of chloro- and bromo- derivatives of N-halosuccinimide, N,N'-dihalo-dimethylhydantoin, sodium or potassium N,N'-dihalocyanurate, trihaloisocyanuric acid, N-halo-2-oxazolidinones and haloglcolurils.

33. The method of claim 32 wherein N,N'-dihalo-2-imidazolidinone is formed in said aqueous medium in amounts sufficient to be biocidally effective against halogen-sensitive microorganisms.

* * * * *